(12) United States Patent
Himmelsbach et al.

(10) Patent No.: US 7,019,012 B2
(45) Date of Patent: Mar. 28, 2006

(54) QUINAZOLINE DERIVATIVES AND PHARMACEUTICAL COMPOSITIONS CONTAINING THEM

(75) Inventors: Frank Himmelsbach, Mittelbiberach (DE); Elke Langkopf, Warthausen (DE); Stefan Blech, Warthausen (DE); Birgit Jung, Schwabenheim (DE); Anke Baum, Alland (AT); Flavio Solca, Vienna (AT)

(73) Assignee: Boehringer Ingelheim International Pharma GmbH & Co. KG, Ingelheim (DE)

(*) Notice: Subject to any disclaimer, the term of this patent is extended or adjusted under 35 U.S.C. 154(b) by 36 days.

(21) Appl. No.: 10/023,099

(22) Filed: Dec. 17, 2001

(65) Prior Publication Data

US 2002/0173509 A1 Nov. 21, 2002

Related U.S. Application Data

(60) Provisional application No. 60/259,201, filed on Dec. 18, 2000.

(30) Foreign Application Priority Data

Dec. 20, 2000 (DE) .......................... 100 63 435

(51) Int. Cl.
A61K 31/5377 (2006.01)
A61K 31/517 (2006.01)
C07D 239/72 (2006.01)
C07D 413/02 (2006.01)

(52) U.S. Cl. .................... 514/266.22; 514/266.24; 514/266.4; 514/217.06; 514/313; 514/314; 544/122; 544/283; 544/284; 544/293

(58) Field of Classification Search ............ 514/266.22, 514/266.24, 266.4, 217.06, 313, 314; 544/122, 544/283, 284, 293

See application file for complete search history.

(56) References Cited

U.S. PATENT DOCUMENTS

| | | | | |
|---|---|---|---|---|
| 5,866,572 | A | * | 2/1999 | Barker et al. ............ 514/234.5 |
| 6,127,374 | A | | 10/2000 | Bridges ...................... 514/259 |
| 6,153,617 | A | | 11/2000 | Bridges ...................... 514/259 |
| 6,251,912 | B1 | | 6/2001 | Wissner et al. ............. 514/259 |
| 6,344,459 | B1 | * | 2/2002 | Bridges et al. .......... 514/234.5 |
| 6,627,634 | B1 | | 9/2003 | Himmelsbach et al. 514/266.22 |
| 6,673,803 | B1 | * | 1/2004 | Thomas et al. .......... 514/263.4 |
| 2001/0044435 | A1 | | 11/2001 | Himmelsbach et al. ..... 514/218 |
| 2002/0032208 | A1 | * | 3/2002 | Lohmann et al. ........... 514/259 |
| 2002/0169180 | A1 | | 11/2002 | Himmelsbach et al. .. 514/266.4 |
| 2003/0149062 | A1 | * | 8/2003 | Jung et al. ............. 514/266.22 |
| 2003/0191308 | A1 | * | 10/2003 | Hennequin et al. ........... 544/60 |
| 2004/0024019 | A1 | * | 2/2004 | Tanimoto et al. ........... 514/314 |
| 2005/0085495 | A1 | * | 4/2005 | Soyka et al. ........... 514/266.24 |

FOREIGN PATENT DOCUMENTS

| | | |
|---|---|---|
| DE | 199 08 567 | 2/1999 |
| DE | 199 11 366 | 3/1999 |
| EP | 566226 | 10/1993 |

(Continued)

OTHER PUBLICATIONS

Tsou, Hwei–Ru, " 6–Substituted–4–(3–bromophenylamino)quinazolines as Putative Irreversible Inhibitors of the Epidermal Growth Factor Receptor (EGFR) and Human Epidermal Growth Factor Receptor (HER–2) Tyrosine Kinases with Enhanced Antitumor Activity",J. Med. Chem., 2001, 2719–2734, vol. 44.

U.S. Appl. No. 10/016,280, Himmelsbach et al., filed Dec. 2001.*

Primary Examiner—James O. Wilson
Assistant Examiner—Tamthom N. Truong
(74) Attorney, Agent, or Firm—Michael P. Morris; Mary-Ellen M. Devlin; Alan Stempel

(57) ABSTRACT

A compound of general formula I

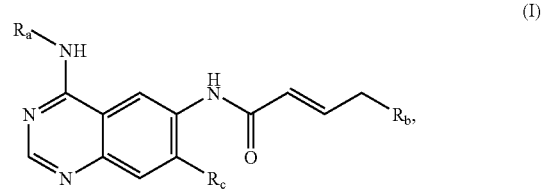

(I)

wherein:

$R_a$ is a benzyl, 1-phenylethyl, or 3-chloro-4-fluorophenyl group;

$R_b$ is a dimethylamino, N-methyl-N-ethylamino, diethylamino, N-methyl-N-isopropylamino, N-methyl-N-cyclopropylamino, N-methyl-N-(2-methoxyethyl) amino, N-ethyl-N-(2-methoxyethyl)amino, bis(2-methoxyethyl)amino, morpholino, N-methyl-N-(tetrahydrofuran-3-yl)amino, N-methyl-N-(tetrahydrofuran-2-ylmethyl)amino, N-methyl-N-(tetrahydrofuran-3-ylmethyl)amino, N-methyl-N-(tetrahydropyran-4-yl)amino, or N-methyl-N-(tetrahydropyran-4-ylmethyl)amino group; and $R_c$ is a cyclopropylmethoxy, cyclobutyloxy, cyclopentyloxy, tetrahydrofuran-3-yloxy, tetrahydrofuran-2-ylmethoxy, tetrahydrofuran-3-ylmethoxy, tetrahydropyran-4-yloxy, or tetrahydropyran-4-ylmethoxy group, or a tautomer, stereoisomer, or salt thereof, particularly the physiologically acceptable salts thereof with inorganic or organic acids or bases which have valuable pharmacological properties, in particular an inhibitory effect on signal transduction mediated by tyrosine kinases, their use in the treatment of diseases, especially tumoral diseases and diseases of the lungs and airways, and the preparation thereof.

6 Claims, No Drawings

FOREIGN PATENT DOCUMENTS

| | | |
|---|---|---|
| WO | WO 95/20045 | 7/1995 |
| WO | WO 96/30347 | 10/1996 |
| WO | WO 96/33980 | 10/1996 |
| WO | WO 97/02266 | 1/1997 |
| WO | WO 97/38983 | 10/1997 |
| WO | WO 98/43960 | 10/1998 |
| WO | WO 99/06378 | 2/1999 |
| WO | WO 99/06396 | 2/1999 |
| WO | 99-09016 * | 2/1999 |
| WO | WO 99/35146 | 7/1999 |
| WO | WO 00/18740 | 4/2000 |
| WO | WO 00/31068 | 6/2000 |
| WO | WO-00/51991 A1 | 9/2000 |
| WO | WO 00/55141 | 9/2000 |
| WO | WO-00/78735 A1 | 12/2000 |
| WO | WO-01/77104 A1 | 10/2001 |

* cited by examiner

QUINAZOLINE DERIVATIVES AND PHARMACEUTICAL COMPOSITIONS CONTAINING THEM

RELATED APPLICATIONS

Benefit under 35 U.S.C. §119(e) of prior provisional application Ser. No. 60/259,201, filed Dec. 18, 2000, is hereby claimed.

SUMMARY OF THE INVENTION

The present invention relates to quinazoline derivatives of general formula

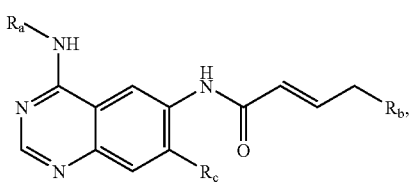

(I)

the tautomers, the stereoisomers and the salts thereof, particularly the physiologically acceptable salts thereof with inorganic or organic acids or bases which have valuable pharmacological properties, particularly an inhibitory effect on signal transduction mediated by tyrosine kinases, the use thereof for treating diseases, particularly tumoral diseases, diseases of the lungs and respiratory tract, and the preparation thereof.

In the above general formula I $R_a$ denotes a benzyl, 1-phenylethyl or 3-chloro-4-fluorophenyl group, $R_b$ denotes a dimethylamino, N-methyl-N-ethylamino, diethylamino, N-methyl-N-isopropylamino, N-methyl-N-cyclopropylamino, N-methyl-N-(2-methoxyethyl) amino, N-ethyl-N-(2-methoxyethyl)amino, bis(2-methoxyethyl)amino, morpholino, N-methyl-N-(tetrahydrofuran-3-yl)amino, N-methyl-N-(tetrahydrofuran-2-ylmethyl)amino, N-methyl-N-(tetrahydrofuran-3-ylmethyl)amino, N-methyl-N-(tetrahydropyran-4-yl)amino or N-methyl-N-(tetrahydropyran-4-ylmethyl)amino group and $R_c$ denotes a cyclopropylmethoxy, cyclobutyloxy, cyclopentyloxy, tetrahydrofuran-3-yloxy, tetrahydrofuran-2-ylmethoxy, tetrahydrofuran-3-ylmethoxy, tetrahydropyran-4-yloxy or tetrahydropyran-4-ylmethoxy group, with the exception of the compounds (1) 3-chloro-4-fluorophenyl)amino]-6-{[4-(N,N-diethylamino)-1-oxo-2-buten-1-yl]amino}-7-cyclopropylmethoxyquinazoline, (2) 4-[(3-chloro-4-fluorophenyl)amino]-6-{[4-(morpholin-4-yl)-1-oxo-2-buten-1-yl]amino}-7-cyclopropylmethoxyquinazoline, (3) 4-[(3-chloro-4-fluorophenyl)amino]-6-{[4-(dimethylamino)-1-oxo-2-buten-1-yl]amino}-7-cyclopropylmethoxyquinazoline, (4) 4-[(3-chloro-4-fluorophenyl)amino]-6-{[4-(morpholin-4-yl)-1-oxo-2-buten-1-yl]amino}-7-cyclobutyloxyquinazoline, (5) 4-[(3-chloro-4-fluorophenyl)amino]-6-{[4-(morpholin-4-yl)-1-oxo-2-buten-1-yl]amino}-7-cyclopentyloxyquinazoline, (6) 4-[(3-chloro-4-fluorophenyl)amino]-6-{[4-(diethylamino)-1-oxo-2-buten-1-yl]amino}7-cyclobutyloxyquinazoline, (7) 4-[(3-chloro-4-fluorophenyl)amino]-6-{[4-(diethylamino)-1-oxo-2-buten-1-yl]amino}7-cyclopentyloxyquinazoline, (8) 4-[(R)-(1-phenylethyl)amino]-6-{[4-(morpholin-4-yl)-1-oxo-2-buten-1-yl]amino}-7-cyclobutyloxyquinazoline, (9) 4-[(R)-(1-phenylethyl)amino]-6-{[4-(morpholin-4-yl)-1-oxo-2-buten-1-yl]amino}-7-cyclopropylmethoxyquinazoline,

(10) 4-[(R)-(1-phenylethyl)amino]-6-{[4-(morpholin-4-yl)-1-oxo-2-buten-1-yl]amino}-7-cyclopentyloxyquinazoline,

(11) 4-[(R)-(1-phenylethyl)amino]-6-{[4-(diethylamino)-1-oxo-2-buten-1-yl]amino}-7-cyclobutyloxyquinazoline,

(12) 4-[(R)-(1-phenylethyl)amino]-6-{[4-(diethylamino)-1-oxo-2-buten-1-yl]amino}-7-cyclopentyloxyquinazoline,

(13) 4-[(R)-(1-phenylethyl)amino]-6-{[4-(diethylamino)-1-oxo-2-buten-1-yl]amino}-7-cyclopropylmethoxyquinazoline,

(14) 4-[(3-chloro-4-fluorophenyl)amino]-6-({4-[bis(2-methoxyethyl)amino]-1-oxo-2-buten-1-yl}amino)-7-cyclopropylmethoxyquinazoline,

(15) 4-[(3-chloro-4-fluorophenyl)amino]-6-({4-[N-ethyl-N-(2-methoxyethyl)amino]-1-oxo-2-buten-1-yl}amino)-7-cyclopropylmethoxyquinazoline,

(16) 4-[(3-chloro-4-fluorophenyl)amino]-6-({4-[N-methyl-N-(tetrahydropyran-4-yl)amino]-1-oxo-2-buten-1-yl}amino)-7-cyclopropylmethoxyquinazoline,

(17) 4-[(3-chloro-4-fluorophenyl)amino]-6-{[4-(diethylamino)-1-oxo-2-buten-1-yl]amino}-7-[(tetrahydrofuran-2-yl)methoxy]quinazoline,

(18) 4-[(3-chloro-4-fluorophenyl)amino]-6-{[4-(diethylamino)-1-oxo-2-buten-1-yl]amino}-7-[(S)-(tetrahydrofuran-3-yl)oxy]quinazoline,

(19) 4-[(3-chloro-4-fluorophenyl)amino]-6-{[4-(diethylamino)-1-oxo-2-buten-1-yl]amino}-7-[(tetrahydropyran-4-yl)oxy]quinazoline,

(20) 4-[(3-chloro-4-fluorophenyl)amino]-6-({4-[N-methyl-N-(tetrahydrofuran-2-ylmethyl)amino]-1-oxo-2-buten-1-yl}amino)-7-cyclopropylmethoxyquinazoline and

(21) 4-[(3-chloro-4-fluorophenyl)amino]-6-({4-[N-methyl-N-(tetrahydrofuran-3-yl)amino]-1-oxo-2-buten-1-yl}amino)-7-cyclopropylmethoxyquinazoline.

Preferred compounds of the above general formula I are those wherein $R_a$, $R_b$, and $R_c$ are as hereinbefore defined, but with the exception of the compounds (1) 4-[(3-chloro-4-fluorophenyl)amino]-6-{[4-(N,N-diethylamino)-1-oxo-2-buten-1-yl]amino}-7-cyclopropylmethoxyquinazoline, (2) 4-[(3-chloro-4-fluorophenyl)amino]-6-{[4-(morpholin-4-yl)-1-oxo-2-buten-1-yl]amino}-7-cyclopropylmethoxyquinazoline, (3) 4-[(3-chloro-4-fluorophenyl)amino]-6-{[4-(dimethylamino)-1-oxo-2-buten-1-yl]amino}-7-cyclopropylmethoxyquinazoline, (4) 4-[(3-chloro-4-fluorophenyl)amino]-6-{[4-(morpholin-4-yl)-1-oxo-2-buten-1-yl]amino}-7-cyclobutyloxyquinazoline, (5) 4-[(3-chloro-4-fluorophenyl)amino]-6-{[4-(morpholin-4-yl)-1-oxo-2-buten-1-yl]amino}-7-cyclopentyloxyquinazoline, (6) 4-[(3-chloro-4-fluorophenyl)amino]-6-{[4-(diethylamino)-1-oxo-2-buten-1-1-yl]amino}-7-cyclobutyloxyquinazoline, (7) 4-[(3-chloro-4-fluorophenyl)amino]-6-{[4-(diethylamino)-1-oxo-2-buten-1-yl]amino}7-cyclopentyloxyquinazoline, (8) 4-[(R)-(1-phenylethyl)amino]-6-{[4-(morpholin-4-yl)-1-oxo-2-buten-1-yl]amino}-7-cyclobutyloxyquinazoline,
(9) 4-[(R)-(1-phenylethyl)amino]-6-{[4-(morpholin-4-yl)-1-oxo-2-buten-1-yl]amino}-7-cyclopropylmethoxyquinazoline,
(10) 4-[(R)-(1-phenylethyl)amino]-6-{[4-(morpholin-4-yl)-1-oxo-2-buten-1-yl]amino}-7-cyclopentyloxyquinazoline,
(11) 4-[(R)-(1-phenylethyl)amino]-6-{[4-(diethylamino)-1-oxo-2-buten-1-yl]amino}-7-cyclobutyloxyquinazoline,
(12) 4-[(R)-(1-phenylethyl)amino]-6-{[4-(diethylamino)-1-oxo-2-buten-1-yl]amino}-7-cyclopentyloxyquinazoline,
(13) 4-[(R)-(1-phenylethyl)amino]-6-{[4-(diethylamino)-1-oxo-2-buten-1-yl]amino}-7-cyclopropylmethoxyquinazoline,
(14) 4-[(3-chloro-4-fluorophenyl)amino]-6-({4-[bis(2-methoxyethyl)amino]-1-oxo-2-buten-1-yl}amino)-7-cyclopropylmethoxyquinazoline,
(15) 4-[(3-chloro-4-fluorophenyl)amino]-6-({4-[N-ethyl-N-(2-methoxyethyl)amino]-1oxo-2-buten-1-yl}amino)-7-cyclopropylmethoxyquinazoline,
(16) 4-[(3-chloro-4-fluorophenyl)amino]-6-({4-[N-methyl-N-(tetrahydropyran-4-yl)amino]-1-oxo-2-buten-1-yl}amino)-7-cyclopropylmethoxyquinazoline,
(17) 4-[(3-chloro-4-fluorophenyl)amino]-6-{[4-(diethylamino)-1-oxo-2-buten-1-yl]amino}-7-[(tetrahydrofuran-2-yl)methoxy]quinazoline,
(18) 4-[(3-chloro-4-fluorophenyl)amino]-6-{[4-(diethylamino)-1-oxo-2-buten-1-yl]amino }-7-[(S)-(tetrahydrofuran-3-yl)oxy]quinazoline,
(19) 4-[(3-chloro-4-fluorophenyl)amino]-6-{[4-(diethylamino)-1-oxo-2-buten-1-1yl]amino}-7-[(tetrahydropyran-4-yl)oxy]quinazoline,
(20) 4-[(3-chloro-4-fluorophenyl)amino]-6-({4-[N-methyl-N-(tetrahydrofuran-2-ylmethyl)amino]-1-oxo-2-buten-1-yl}amino)-7-cyclopropylmethoxyquinazoline,
(21) 4-[(3-chloro-4-fluorophenyl)amino]-6-({4-[N-methyl-N-(tetrahydrofuran-3-yl)amino]-1-oxo-2-buten-1-yl}amino)-7-cyclopropylmethoxyquinazoline,
(22) 4-[(3-chloro-4-fluorophenyl)amino]-6-({4-[N-(2-methoxyethyl)-N-methylamino]-1-oxo-2-buten-1-yl}amino)-7-cyclopropylmethoxyquinazoline,
(23) 4-[(3-chloro-4-fluorophenyl)amino]-6-({4-[bis(2-methoxyethyl)amino]-1-oxo-2-buten-1-yl}amino)-7-cyclobutyloxyquinazoline,
(24) 4-[(3-chloro-4-fluorophenyl)amino]-6-({4-[N-methyl-N-(2-methoxyethyl)amino]-1-oxo-2-buten-1-yl}amino)-7-cyclobutyloxyquinazoline,
(25) 4-[(3-chloro-4-fluorophenyl)amino]-6-({4-[(S)-N-methyl-N-(tetrahydrofuran-3-yl)amino]-1-oxo-2-buten-1-yl}amino)-7-cyclobutyloxyquinazoline,
(26) 4-[(3-chloro-4-fluorophenyl)amino]-6-({4-[(R)-N-methyl-N-(tetrahydrofuran-3-yl)amino]-1-oxo-2-buten-1-yl}amino)-7-cyclobutyloxyquinazoline,
(27) 4-[(3-chloro-4-fluorophenyl)amino]-6-({4-[N-methyl-N-(tetrahydropyran-4-yl)amino]-1-oxo-2-buten-1-yl}amino)-7-cyclobutyloxyquinazoline,
(28) 4-[(3-chloro-4-fluorophenyl)amino]-6-({4-[(R)-N-methyl-N-(tetrahydrofuran-2-ylmethyl)amino]-1-oxo-2-buten-1-yl]-amino)-7-cyclobutyloxyquinazoline,
(29) 4-[(3-chloro-4-fluorophenyl)amino]-6-({4-[(S)-N-methyl-N-(tetrahydrofuran-2-ylmethyl)amino]-1-oxo-2-buten-1-yl]-amino)-7-cyclobutyloxyquinazoline,
(30) 4-[(3-chloro-4-fluorophenyl)amino]-6-({4-[N-methyl-N-(2-methoxyethyl)amino]-1-oxo-2-buten-1-yl}amino)-7-(tetrahydrofuran-3-yloxy)quinazoline,
(31) 4-[(3-chloro-4-fluorophenyl)amino]-6-({4-[N-methyl-N-(2-methoxyethyl)amino]-1-oxo-2-buten-1-yl}amino)-7-(tetrahydropyran-4-yloxy)quinazoline,
(32) 4-[(3-chloro-4-fluorophenyl)amino]-6-({4-[N-methyl-N-(2-methoxyethyl)amino]-1-oxo-2-buten-1-yl}amino)-7-(tetrahydrofuran-2-ylmethoxy)quinazoline and
(33) 4-[(3-chloro-4-fluorophenyl)amino]-6-{[4-(N-cyclopropyl-N-methylamino)-1-oxo-2-buten-1-yl]amino}-7-cyclopropylmethoxyquinazoline, the tautomers, the stereoisomers and the salts thereof.

Particularly preferred compounds of general formula I are those wherein $R_a$ denotes a 1-phenylethyl or 3-chloro-4-fluorophenyl group, $R_b$ denotes a dimethylamino, N-methyl-N-ethylamino, diethylamino, N-methyl-N-isopropylamino, N-methyl-N-cyclopropylamino, N-methyl-N-(2-methoxyethyl)amino, N-ethyl-N-(2-methoxyethyl)amino, bis(2-methoxyethyl)amino, morpholino, N-methyl-N-(tetrahydrofuran-3-yl)amino, N-methyl-N-(tetrahydrofuran-2-ylmethyl)amino, N-methyl-N-(tetrahydrofuran-3-ylmethyl)amino, N-methyl-N-(tetrahydropyran-4-yl)amino or N-methyl-N-(tetrahydropyran-4-ylmethyl)amino group and $R_c$ denotes a cyclopropylmethoxy, cyclobutyloxy, cyclopentyloxy, tetrahydrofuran-3-yloxy, tetrahydrofuran-2-ylmethoxy, tetrahydrofuran-3-ylmethoxy, tetrahydropyran-4-yloxy or tetrahydropyran-4-ylmethoxy group, with the exception of the compounds (1) 4-[(3-chloro-4-fluorophenyl)amino]-6-{[4-(N,N-diethylamino)-1-oxo-2-buten-1-yl]amino}-7-cyclopropylmethoxyquinazoline,
(2) 4-[(3-chloro-4-fluorophenyl)amino]-6-{[4-(morpholin-4-yl)-1-oxo-2-buten-1-yl]amino}-7-cyclopropylmethoxyquinazoline,
(3) 4-[(3-chloro-4-fluorophenyl)amino]-6-{[4-(dimethylamino)-1-oxo-2-buten-1-yl]amino}-7-cyclopropylmethoxyquinazoline,
(4) 4-[(3-chloro-4-fluorophenyl)amino]-6-{[4-(morpholin-4-yl)-1-oxo-2-buten-1-yl]amino}-7-cyclobutyloxyquinazoline,
(5) 4-[(3-chloro-4-fluorophenyl)amino]-6-{[4-(morpholin-4-yl)-1-oxo-2-buten-1-yl]amino}-7-cyclopentyloxyquinazoline,
(6) 4-[(3-chloro-4-fluorophenyl)amino]-6-{[4-(diethylamino)-1-oxo-2-buten-1-yl]amino}7-cyclobutyloxyquinazoline,
(7) 4-[(3-chloro-4-fluorophenyl)amino]-6-{[4-(diethylamino)-1-oxo-2-buten-1-yl]amino}-7-cyclopentyloxyquinazoline,
(8) 4-[(R)-(1-phenylethyl)amino]-6-{[4-(morpholin-4-yl)-1-oxo-2-buten-1-yl]amino}-7-cyclobutyloxyquinazoline,
(9) 4-[(R)-(1-phenylethyl)amino]-6-{[4-(morpholin-4-yl)-1-oxo-2-buten-1-yl]amino}7-cyclopropylmethoxyquinazoline,
(10) 4-[(R)-(1-phenylethyl)amino]-6-{[4-(morpholin-4-yl)-1-oxo-2-buten-1-yl]amino}-7-cyclopentyloxyquinazoline,
(11) 4-[(R)-(1-phenylethyl)amino]-6-{[4-(diethylamino)-1-oxo-2-buten-1-yl]amino}-7-cyclobutyloxyquinazoline,
(12) 4-[(R)-(1-phenylethyl)amino]-6-{[4-(diethylamino)-1-oxo-2-buten-1-yl]amino}-7-cyclopentyloxyquinazoline,
(13) 4-[(R)-(1-phenylethyl)amino]-6-{[4-(diethylamino)-1-oxo-2-buten-1-yl]amino}-7-cyclopropylmethoxyquinazoline,
(14) 4-[(3-chloro-4-fluorophenyl)amino]-6-({4-[bis(2-methoxyethyl)amino]-1-oxo-2-buten-1-yl}amino)-7-cyclopropylmethoxyquinazoline,
(15) 4-[(3-chloro-4-fluorophenyl)amino]-6-({4-[N-ethyl-N-(2-methoxyethyl)amino]-1-oxo-2-buten-1-yl}amino)-7-cyclopropylmethoxyquinazoline,

(16) 4-[(3-chloro-4-fluorophenyl)amino]-6-({4-[N-methyl-N-(tetrahydropyran-4-yl)amino]-1-oxo-2-buten-1-yl}amino)-7-cyclopropylmethoxyquinazoline,
(17) 4-[(3-chloro-4-fluorophenyl)amino]-6-{[4-(diethylamino)-1-oxo-2-buten-1-yl]amino}-7-[(tetrahydrofuran-2-yl)methoxy]quinazoline,
(18) 4-[(3-chloro-4-fluorophenyl)amino]-6-{[4-(diethylamino)-1-oxo-2-buten-1-yl]amino}-7-[(S)-(tetrahydrofuran-3-yl)oxy]quinazoline,
(19) 4-[(3-chloro-4-fluorophenyl)amino]-6-{[4-(diethylamino)-1-oxo-2-buten-1-yl]amino}-7-[(tetrahydropyran-4-yl)oxy]quinazoline,
(20) 4-[(3-chloro-4-fluorophenyl)amino]-6-({4-[N-methyl-N-(tetrahydrofuran-3-yl)amino]-1-oxo-2-buten-1-yl}amino)-7-cyclopropylmethoxyquinazoline,
(21) 4-[(3-chloro-4-fluorophenyl)amino]-6-({4-[N-(2-methoxyethyl)-N-methylamino]-1-oxo-2-buten-1-yl}amino)-7-cyclopropylmethoxyquinazoline,
(22) 4-[(3-chloro-4-fluorophenyl)amino]-6-({4-[bis(2-methoxyethyl)amino]-1-oxo-2-buten-1-yl}amino)-7-cyclobutyloxyquinazoline,
(23) 4-[(3-chloro-4-fluorophenyl)amino]-6-({4-[N-methyl-N-(2-methoxyethyl)amino]-1-oxo-2-buten-1-yl}amino)-7-cyclobutyloxyquinazoline,
(24) 4-[(3-chloro-4-fluorophenyl)amino]-6-({4-[(S)-N-methyl-N-(tetrahydrofuran-3-yl)amino]-1-oxo-2-buten-1-yl}amino)-7-cyclobutyloxyquinazoline,
(25) 4-[(3-chloro-4-fluorophenyl)amino]-6-({4-[(R)-N-methyl-N-(tetrahydrofuran-3-yl)amino]-1-oxo-2-buten-1-yl}amino)-7-cyclobutyloxyquinazoline,
(26) 4-[(3-chloro-4-fluorophenyl)amino]-6-({4-[N-methyl-N-(tetrahydropyran-4-yl)amino]-1-oxo-2-buten-1-yl}amino)-7-cyclobutyloxyquinazoline,
(27) 4-[(3-chloro-4-fluorophenyl)amino]-6-({4-[N-methyl-N-(2-methoxyethyl)amino]-1-oxo-2-buten-1-yl}amino)-7-(tetrahydrofuran-3-yloxy)quinazoline,
(28) 4-[(3-chloro-4-fluorophenyl)amino]-6-({4-[N-methyl-N-(2-methoxyethyl)amino]-1-oxo-2-buten-1-yl}amino)-7-(tetrahydropyran-4-yloxy)quinazoline,
(29) 4-[(3-chloro-4-fluorophenyl)amino]-6-({4-[N-methyl-N-(2-methoxyethyl)amino]-1-oxo-2-buten-1-yl}amino)-7-(tetrahydrofuran-2-ylmethoxy)quinazoline,
(30) 4-[(3-chloro-4-fluorophenyl)amino]-6-{[4-(N-cyclopropyl-N-methylamino)-1-oxo-2-buten-1-yl]amino}-7-cyclopropylmethoxyquinazoline,
(31) 4-[(3-chloro-4-fluorophenyl)amino]-6-({4-[N-methyl-N-(tetrahydrofuran-2-ylmethyl)amino]-1-oxo-2-buten-1-yl}amino)-7-cyclopropylmethoxyquinazoline,
(32) 4-[(3-chloro-4-fluorophenyl)amino]-6-({4-[(R)-N-methyl-N-(tetrahydrofuran-2-ylmethyl)amino]-1-oxo-2-buten-1-yl}-amino)-7-cyclobutyloxyquinazoline and
(33) 4-[(3-chloro-4-fluorophenyl)amino]-6-({4-[(S)-N-methyl-N-(tetrahydrofuran-2-ylmethyl)amino]-1-oxo-2-buten-1-yl}-amino)-7-cyclobutyloxyquinazoline,
the tautomers, the stereoisomers and the salts thereof.

The following particularly preferred compounds of general formula I may be mentioned by way of example:
(a) 4-[(3-chloro-4-fluorophenyl)amino]-6-{[4-(N,N-dimethylamino)-1-oxo-2-buten-1-yl]amino}-7-cyclobutyloxyquinazoline;
(b) 4-[(3-chloro-4-fluorophenyl)amino]-6-{[4-(N,N-dimethylamino)-1-oxo-2-buten-1-yl]amino}-7-cyclopentyloxyquinazoline,
(c) 4-[(R)-(1-phenylethyl)amino]-6-{[4-(N,N-bis(2-methoxyethyl)amino)-1-oxo-2-buten-1-yl]amino}-7-cyclopropylmethoxyquinazoline,
(d) 4-[(R)-(1-phenylethyl)amino]-6-({4-[N-(2-methoxyethyl)-N-ethylamino]-1-oxo-2-buten-1-yl}amino)-7-cyclopropylmethoxyquinazoline,
(e) 4-[(R)-(1-phenylethyl)amino]-6-({4-[N-(2-methoxyethyl)-N-methylamino]-1-oxo-2-buten-1-yl}amino)-7-cyclopropylmethoxyquinazoline,
(f) 4-[(R)-(1-phenylethyl)amino]-6-({4-[N-(tetrahydropyran-4-yl)-N-methylamino]-1-oxo-2-buten-1-yl}amino)-7-cyclopropylmethoxyquinazoline,
(g) 4-[(R)-(1-phenylethyl)amino]-6-({4-[N-(tetrahydrofuran-3-yl)-N-methylamino]-1-oxo-2-buten-1-yl}amino)-7-cyclopropylmethoxyquinazoline,
(h) 4-[(3-chloro-4-fluorophenyl)amino]-6-[(4-{N-[(tetrahydrofuran-3-yl)methyl]-N-methylamino}-1-oxo-2-buten-1-yl)amino]-7-cyclopropylmethoxyquinazoline,
(i) 4-[(3-chloro-4-fluorophenyl)amino]-6-{[4-(N,N-dimethylamino)-1-oxo-2-buten-1-yl]amino}-7-((R)-tetrahydrofuran-3-yloxy)quinazoline,
(j) 4-[(3-chloro-4-fluorophenyl)amino]-6-{[4-(N,N-dimethylamino)-1-oxo-2-buten-1-yl]amino}-7-((S)-tetrahydrofuran-3-yloxy)quinazoline,
(k) 4-[(3-chloro-4-fluorophenyl)amino]-6-{[4-(N,N-dimethylamino)-1-oxo-2-buten-1-yl]amino}-7-(tetrahydropyran-4-yloxy)quinazoline,
(l) 4-[(3-chloro-4-fluorophenyl)amino]-6-{[4-(N,N-dimethylamino)-1-oxo-2-buten-1-yl]amino}-7-[(tetrahydrofuran-2-yl)methoxy]quinazoline,
(m) 4-[(3-chloro-4-fluorophenyl)amino]-6-{[4-(N,N-dimethylamino)-1-oxo-2-buten-1-yl]amino}-7-[(tetrahydrofuran-3-yl)methoxy]quinazoline,
(o) 4-[(3-chloro-4-fluorophenyl)amino]-6-{[4-(N,N-diethylamino)-1-oxo-2-buten-1-yl]amino}7-[(tetrahydrofuran-3-yl)methoxy]quinazoline,
(p) 4-[(R)-(1-phenylethyl)amino]-6-{[4-(N,N-dimethylamino)-1-oxo-2-buten-1-yl]amino}7-cyclopropylmethoxyquinazoline,
(q) 4-[(3-chloro-4-fluorophenyl)amino]-6-({4-[N,N-bis(2-methoxyethyl)amino]-1-oxo-2-buten-1-yl}amino)-7-[(tetrahydrofuran-2-yl)methoxy]quinazoline,
(r) 4-[(3-chloro-4-fluorophenyl)amino]-6-{[4-(morpholin-4-yl)-1-oxo-2-buten-1-yl]amino }-7-[(tetrahydrofuran-2-yl)methoxy]quinazoline,
(s) 4-[(3-chloro-4-fluorophenyl)amino]-6-{[4-(N-cyclopropyl-N-methylamino)-1-oxo-2-buten-1-yl]amino}-7-cyclopentyloxyquinazoline; and
(t) 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]quinazoline,
the tautomers, the stereoisomers and the salts thereof.

The compounds of general formula I may be prepared by the following methods, for example:

a) reacting a compound of general formula

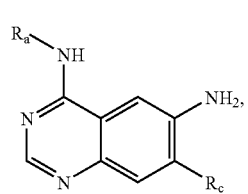

(II)

wherein:

$R_a$ and $R_c$ are as hereinbefore defined, with a compound of general formula

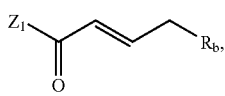

wherein:

R$_b$ is as hereinbefore defined; and

Z$_1$ denotes a leaving group such as a halogen atom, e.g., a chlorine or bromine atom, or a hydroxy group.

The reaction is optionally carried out in a solvent or mixture of solvents such as methylene chloride, dimethylformamide, benzene, toluene, chlorobenzene, tetrahydrofuran, benzene/tetrahydrofuran or dioxane, optionally in the presence of an inorganic or organic base and optionally in the presence of a dehydrating agent, expediently at temperatures between −50° C. and 150° C., preferably at temperatures between −20° C. and 80° C.

With a compound of general formula III wherein Z$_1$ denotes a leaving group, the reaction is optionally carried out in a solvent or mixture of solvents such as methylene chloride, dimethylformamide, benzene, toluene, chlorobenzene, tetrahydrofuran, benzene/tetrahydrofuran or dioxane, conveniently in the presence of a tertiary organic base such as triethylamine, pyridine or 4-dimethylaminopyridine, in the presence of N-ethyldiisopropylamine (Hünig base), whilst these organic bases may simultaneously also act as solvent, or in the presence of an inorganic base such as sodium carbonate, potassium carbonate or sodium hydroxide solution, expediently at temperatures between −50° C. and 150° C., preferably at temperatures between −20° C. and 80° C.

With a compound of general formula III wherein Z$_1$ denotes a hydroxy group, the reaction is preferably carried out in the presence of a dehydrating agent, e.g., in the presence of isobutyl chloroformate, thionyl chloride, trimethyl chlorosilane, phosphorus trichloride, phosphorus pentoxide, hexamethyldisilazane, N,N'-dicyclohexylcarbodiimide, N,N'-dicyclohexylcarbodiimide/N-hydroxysuccinimide, 1-hydroxybenzotriazole, N,N'-carbonyldiimidazole or triphenylphosphine/carbon tetrachloride, expediently in a solvent such as methylene chloride, tetrahydrofuran, dioxane, toluene, chlorobenzene, dimethylformamide, dimethylsulfoxide, ethylene glycol diethylether or sulfolane and optionally in the presence of a reaction accelerator such as 4-dimethylaminopyridine at temperatures between −50° C. and 150° C., but preferably at temperatures between −20° C. and 80° C.

b) Reacting a compound of general formula

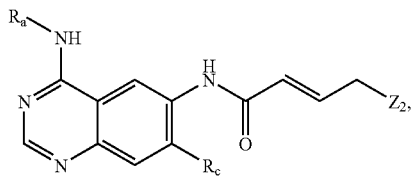

wherein:

R$_a$ and R$_c$ are as hereinbefore defined; and

Z$_2$ denotes a leaving group such as a halogen atom, a substituted hydroxy or sulfonyloxy group such as a chlorine or bromine atom, a methanesulfonyloxy or p-toluenesulfonyloxy group, with a compound of general formula:

H—R$_b$ (V)

wherein R$_b$ is as hereinbefore defined.

The reaction is expediently carried out in a solvent such as isopropanol, butanol, tetrahydrofuran, dioxane, toluene, chlorobenzene, dimethylformamide, dimethylsulfoxide, methylene chloride, ethylene glycol monomethylether, ethylene glycol diethylether or sulfolane or mixtures thereof, optionally in the presence of an inorganic or tertiary organic base, e.g., sodium carbonate or potassium hydroxide, a tertiary organic base, e.g., triethylamine or N-ethyldiisopropylamine (Hünig base), whilst these organic bases may simultaneously also serve as solvent, and optionally in the presence of a reaction accelerator such as an alkali metal halide at temperatures between −20° C. and 150° C., but preferably at temperatures between −10° C. and 100° C. The reaction may, however, also be carried out without a solvent or in an excess of the compound of general formula V used.

In the reactions described above, the secondary amino group bound to the quinazoline of general formula II or IV may be protected during the reaction by conventional protecting groups which are cleaved again after the reaction. Examples of protecting groups include the formyl, acetyl, trifluoroacetyl, ethoxycarbonyl, tert-butoxycarbonyl, benzyloxycarbonyl, benzyl, methoxybenzyl, or 2,4-dimethoxybenzyl group.

Any protecting group used is optionally subsequently cleaved for example by hydrolysis in an aqueous solvent, e.g., in water, isopropanol/water, acetic acid/water, tetrahydrofuran/water or dioxane/water, in the presence of an acid such as trifluoroacetic acid, hydrochloric acid or sulfuric acid or in the presence of an alkali metal base such as sodium hydroxide or potassium hydroxide or aprotically, e.g., in the presence of iodotrimethylsilane, at temperatures between 0° C. and 120° C., preferably at temperatures between 10° C. and 100° C.

However, a benzyl, methoxybenzyl or benzyloxycarbonyl group is cleaved, for example hydrogenolytically, e.g., with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0° C. and 100° C., but preferably at ambient temperatures between 20° C. and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert-butyl or tert-butyloxycarbonyl group is preferably cleaved by treating with an acid such as trifluoroacetic acid or hydrochloric acid or by treating with iodotrimethylsilane, optionally using a solvent such as methylene chloride, dioxane, methanol or diethyl ether.

A trifluoroacetyl group is preferably cleaved by treating with an acid such as hydrochloric acid, optionally in the presence of a solvent such as acetic acid at temperatures between 50° C. and 120° C. or by treating with sodium hydroxide solution optionally in the presence of a solvent such as tetrahydrofuran at temperatures between 0° C. and 50° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures obtained may be resolved by chromatography into the cis and trans isomers thereof, the compounds of general formula I obtained which occur as racemates may be separated by methods known per se (cf N. L. Allinger and E. L. Eliel in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g., by chromatography and/or fractional crystallization, and, if these compounds are obtained in racemic form, they may subsequently be resolved into the enantiomers as mentioned above.

The enantiomers are preferably separated by column separation on chiral phases or by recrystallization from an optically active solvent or by reacting with an optically active substance which forms salts or derivatives such as, e.g., esters or amides with the racemic compound, particularly acids and the activated derivatives or alcohols thereof, and separating the diastereomeric mixture of salts or derivatives thus obtained, e.g., on the basis of their differences in solubility, whilst the free antipodes may be released from the pure diastereomeric salts or derivatives by the action of suitable agents. Optically active acids in common use are, e.g., the D- and L-forms of tartaric acid or dibenzoyltartaric acid, di-o-tolyltartaric acid, malic acid, mandelic acid, camphorsulfonic acid, glutamic acid, aspartic acid or quinic acid. An optically active alcohol may be for example (+) or (−)-menthol and an optically active acyl group in amides, for example, may be a (+)-or (−)-menthyloxycarbonyl.

Furthermore, the compounds of formula I obtained may be converted into the salts thereof, particularly for pharmaceutical use into the physiologically acceptable salts with inorganic or organic acids. Acids which may be used for this purpose include for example hydrochloric acid, hydrobromic acid, sulfuric acid, methanesulfonic acid, phosphoric acid, fumaric acid, succinic acid, lactic acid, citric acid, tartaric acid, or maleic acid.

The compounds of general formulae II to V used as starting materials are known from the literature in some cases or may be obtained by methods known from the literature.

For example, a starting compound of general formula II is obtained by reacting a 7-fluoro-6-nitro compound correspondingly substituted in the 4 position with a corresponding alkoxide and subsequently reducing the nitro compound thus obtained or a starting compound of general formula III is obtained, for example, by reacting a suitable bromocrotonic acid derivative with one of the amines of general formula V known from the literature, or a starting compound of general formula IV is obtained by acylating a compound of general formula II with a suitable crotonic acid derivative.

As already mentioned hereinbefore, the compounds of general formula I according to the invention and the physiologically acceptable salts thereof have valuable pharmacological properties, particularly an inhibiting effect on signal transduction mediated by the Epidermal Growth Factor receptor (EGF-R), whilst this may be achieved for example by inhibiting ligand bonding, receptor dimerization or tyrosine kinase itself. It is also possible to block the transmission of signals to components located further down.

The biological properties of the new compounds were investigated as follows:

The inhibition of human EGF-receptor kinase was determined using the cytoplasmic tyrosine kinase domain (methionine 664 to alanine 1186, based on the sequence published in Nature 309 (1984), 418). To do this, the protein was expressed in Sf9 insect cells as a GST fusion protein using the Baculovirus expression system.

The enzyme activity was measured in the presence or absence of the test compounds in serial dilutions. The polymer pEY (4:1) produced by SIGMA was used as the substrate. Biotinylated pEY (bio-pEY) was added as the tracer substrate. Every 100 µl of reaction solution contained 10 µl of the inhibitor in 50% DMSO, 20 µl of the substrate solution (200 mM HEPES pH 7.4, 50 mM magnesium acetate, 2.5 mg/ml poly(EY), 5 µg/ml bio-pEY) and 20 µl of enzyme preparation. The enzyme reaction was started by the addition of 50 µl of a 100 µM ATP solution in 10 mM magnesium chloride. The dilution of the enzyme preparation was adjusted so that the incorporation of phosphate into the bio-pEY was linear in terms of time and quantity of enzyme. The enzyme preparation was diluted in 20 mM HEPES pH 7.4, 1 mM EDTA, 130 mM common salt, 0.05% Triton X-100, 1 mM DTT and 10% glycerol.

The enzyme assays were carried out at ambient temperature over a period of 30 minutes and were ended by the addition of 50 µl of a stopping solution (250 mM EDTA in 20 mM HEPES pH 7.4). 100 µl were placed on a streptavidin-coated microtiter plate and incubated for 60 minutes at ambient temperature. Then the plate was washed with 200 µl of a washing solution (50 mM Tris, 0.05% Tween 20). After the addition of 100 µl of a HRPO-labelled anti-PY antibody (PY20H Anti-PTyr:HRP produced by Transduction Laboratories, 250 ng/ml), it was incubated for 60 minutes. Then the microtiter plate was washed three times with 200 µl of washing solution. The samples were then combined with 100 µl of a TMB-peroxidase solution (A:B=1:1, Kirkegaard Perry Laboratories). After 10 minutes, the reaction was stopped. The extinction was measured at $OD_{450\ nm}$ with an ELISA reader. All data points were measured three times.

The data were matched by means of an iterative calculation using an analytical program for sigmoidal curves (Graph Pad Prism Version 3.0) with variable Hill pitch. All the iteration data released showed a correlation coefficient of more 0.9 and the upper and lower values of the curves showed a spread of at least a factor of 5. The concentration of active substance which inhibits the activity of EGF-receptor kinase by 50% ($IC_{50}$) was derived from the curves.

The following results were obtained:

| Compound (Example No.) | Inhibition of EGF-Receptor Kinase $IC_{50}$ [nM] |
| --- | --- |
| 1 | 0.7 |
| 1 (2) | 0.6 |
| 1 (3) | 4.0 |
| 1 (5) | 3.0 |
| 1 (10) | 0.5 |
| 1 (22) | 1.0 |
| 1 (32) | 0.3 |
| 1 (33) | 0.5 |
| 1 (34) | 0.4 |

The compounds of general formula I according to the invention thus inhibit signal transduction by tyrosine kinases, as demonstrated by the example of the human EGF receptor, and are therefore useful for treating pathophysiological processes caused by hyperfunction of tyrosine kinases. These are, e.g., benign or malignant tumors, particularly tumors of epithelial and neuroepithelial origin, metastasization and the abnormal proliferation of vascular endothelial cells (neoangiogenesis).

The compounds according to the invention are also useful for preventing and treating diseases of the airways and lungs which are accompanied by increased or altered production of mucus caused by stimulation by tyrosine kinases, e.g., in inflammatory diseases of the airways such as chronic bronchitis, chronic obstructive bronchitis, asthma, bronchiectasis, allergic or non-allergic rhinitis or sinusitis, cystic fibrosis, α1-antitrypsin deficiency, or coughs, pulmonary emphysema, pulmonary fibrosis and hyperreactive airways.

The compounds are also suitable for treating diseases of the gastrointestinal tract and bile duct and gall bladder which are associated with disrupted activity of the tyrosine kinases, such as may be found, e.g., in chronic inflammatory changes such as cholecystitis, Crohn's disease, ulcerative colitis, and ulcers in the gastrointestinal tract or such as may occur in diseases of the gastrointestinal tract which are associated with increased secretions, such as Menetrier's disease, secreting adenomas and protein loss syndrome.

In addition, the compounds of general formula I and the physiologically acceptable salts thereof may be used to treat other diseases caused by abnormal function of tyrosine kinases, such as, e.g., epidermal hyperproliferation (psoriasis), inflammatory processes, diseases of the immune system, hyperproliferation of hematopoietic cells, etc.

By reason of their biological properties the compounds according to the invention may be used on their own or in conjunction with other pharmacologically active compounds, for example in tumour therapy, in monotherapy or in conjunction with other anti-tumour therapeutic agents, for example in combination with topoisomerase inhibitors (e.g., etoposide), mitosis inhibitors (e.g., vinblastine), compounds which interact with nucleic acids (e.g., cis-platin, cyclophosphamide, adriamycin), hormone antagonists (e.g., tamoxifen), inhibitors of metabolic processes (e.g., 5-FU etc.), cytokines (e.g., interferons), antibodies, etc. For treating respiratory tract diseases, these compounds may be used on their own or in conjunction with other therapeutic agents for the airways, such as substances with a secretolytic, broncholytic and/or anti-inflammatory activity. For treating diseases in the region of the gastrointestinal tract, these compounds may also be administered on their own or in conjunction with substances having an effect on motility or secretion. These combinations may be administered either simultaneously or sequentially.

These compounds may be administered either on their own or in conjunction with other active substances by intravenous, subcutaneous, intramuscular, intraperitoneal or intranasal route, by inhalation or transdermally or orally, whilst aerosol formulations are particularly suitable for inhalation.

For pharmaceutical use the compounds according to the invention are generally used for warm-blooded vertebrates, particularly humans, in doses of 0.01–100 mg/kg of body weight, preferably 0.1–15 mg/kg. For administration they are formulated with one or more conventional inert carriers and/or diluents, e.g., with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fatty substances such as hard fat or suitable mixtures thereof in conventional galenic preparations such as plain or coated tablets, capsules, powders, suspensions, solutions, sprays or suppositories.

The following Examples are intended to illustrate the present invention without restricting it.
Preparation of the Starting Compounds

EXAMPLE I 3-methylaminotetrahydrofuran 3.43 g of lithium aluminium hydride are added batchwise to 50 ml of tetrahydrofuran while cooling with an ice bath. Then a solution of 5.00 g of 3-[(benzyloxycarbonyl)-amino] tetrahydrofuran in 20 ml tetrahydrofuran is added dropwise, while the temperature remains below 10° C. After 10 minutes, the cooling bath is removed and the reaction mixture is refluxed for about three hours. For working up, 3.7 ml of water, 3.7 ml of 15% sodium hydroxide solution, and another 3 ml of water are carefully added dropwise to the reaction mixture while cooling with an ice bath. Then some tetrahydrofuran is added and the mixture is stirred for another 15 minutes. The aluminium hydroxide slurry precipitated is suction filtered and washed with a total of 150 ml of tetrahydrofuran. The filtrate is evaporated down using the rotary evaporator. A colorless oil remains, which is reacted without any further purification. Mass spectrum (ESI$^+$): m/z=102 [M+H]$^+$; $R_f$ value: 0.20 (silica gel, methylene chloride/methanol=9:1).

EXAMPLE II

3-[(benzyloxycarbonyl)amino]tetrahydrofuran 12.36 ml of tetrahydrofuran-3-carboxylic acid and 27.84 ml of diphenylphosphorylazide in 500 ml of dioxane are combined with 41.91 g of benzyl alcohol and 35.81 ml of triethylamine. The reaction mixture is heated to 100° C. for about seven hours. After cooling to ambient temperature, the reaction mixture is evaporated down using the rotary evaporator. The residue is taken up in 500 ml of methylene chloride and washed twice with 100 ml of 1 N sodium hydroxide solution. The organic phase is dried over magnesium sulfate and evaporated down. The crude product is purified by chromatography over a silica gel column with cyclohexane/ethyl acetate (3:1 to 1:2) as eluant. Yield: 15.60 g (55% of theory); mass spectrum (ESI$^-$): m/z=220 [M–H]$^-$; $R_f$ value: 0.78 (silica gel, methylene chloride/methanol=9:1).

EXAMPLE III

6-Amino-4-[(3-chloro-4-fluorophenyl)amino]-7-((R)-tetrahydrofuran-3-yloxy)quinazoline A mixture of 12.80 g of 4-[(3-chloro-4-fluorophenyl)amino]-6-nitro-7-((R)-tetrahydrofuran-3-yloxy)quinazoline, 200 ml of ethanol, 100 ml of water, and 17.20 ml of glacial acetic acid is heated to reflux temperature. Then a total of 7.00 g of iron powder is added in batches. The reaction mixture is refluxed for about four hours and then cooled to ambient temperature overnight. For working up, the reaction mixture is evaporated using the rotary evaporator. The residue is taken up in methylene chloride/methanol (9:1), mixed with 20 ml of concentrated ammonia solution and filtered through a layer of silica gel. It is washed with copious amounts of methylene chloride/methanol (9:1) and the combined filtrates are evaporated down. The residue is stirred with diethylether and suction filtered. Yield: 8.59 g (73% of theory); mass spectrum (ESI$^-$): m/z=373, 375 [M–H]$^-$; $R_f$ value: 0.27 (silica gel, ethyl acetate/methanol=9:1).

The following compounds are obtained analogously to Example III:

(1) 6-Amino-4-[(3-chloro-4-fluorophenyl)amino]-7-((S)-tetrahydrofuran-3-yloxy)quinazoline Mass spectrum (ESI$^-$): m/z=373, 375 [M–H]$^-$; $R_f$ value: 0.27 (silica gel, ethyl acetate/methanol=9:1).

(2) 6-Amino-4-[(3-chloro-4-fluorophenyl)amino]-7-(tetrahydropyran-4-yloxy)quinazoline Mass spectrum (ESI$^-$): m/z=387, 389 [M–H]$^-$; $R_f$ value: 0.20 (silica gel, ethyl acetate).

(3) 6-Amino-4-[(3-chloro-4-fluorophenyl)amino]-7-[(tetrahydrofuran-2-yl)methoxy]quinazoline Mass spectrum (ESI$^-$): m/z=387, 389 [M–H]$^-$; $R_f$ value: 0.55 (silica gel, ethyl acetate/methanol=9:1).

(4) 6-Amino-4-[(3-chloro-4-fluorophenyl)amino]-7-[(tetrahydrofuran-3-yl)methoxy]quinazoline Mass spectrum (ESI⁻): m/z=387, 389 [M–H]⁻; $R_f$ value: 0.40 (silica gel, ethyl acetate/methanol=9:1).

EXAMPLE IV
4-[(3-chloro-4-fluorophenyl)amino]-6-nitro-7-((R)-tetrahydrofuran-3-yloxy)quinazoline 13.80 g of potassium tert-butoxide are added batchwise to a solution of 10.80 g of (R)-3-hydroxytetrahydrofuran in 100 ml of N,N-dimethylformamide while cooling with an ice bath. The reaction mixture is stirred for about one hour, then 10.40 g of 4-[(3-chloro-4-fluorophenyl)amino]-6-nitro-7-fluoroquinazoline are added batchwise. The cooling bath is then removed and the deep red reaction mixture is stirred for two hours at ambient temperature. For working up the reaction mixture is poured onto about 500 ml of water and neutralized with 2 N hydrochloric acid. The yellowish precipitate formed is suction filtered and dried at 70° C. in a circulating air drier. Yield: 12.80 g; melting point: 244° C.; mass spectrum (ESI⁻): m/z=403, 405 [M–H]⁻.

The following compounds are obtained analogously to Example IV:
(1) 4-[(3-chloro-4-fluorophenyl)amino]-6-nitro-7-((S)-tetrahydrofuran-3-yloxy)quinazoline Mass spectrum (ESI⁻): m/z=403, 405 [M–H]⁻; $R_f$ value: 0.45 (silica gel, ethyl acetate).
(2) 4-[(3-chloro-4-fluorophenyl)amino]-6-nitro-7-(tetrahydropyran-4-yloxy)quinazoline Mass spectrum (ESI⁻): m/z=417, 419 [M–H]⁻; $R_f$ value: 0.42 (silica gel, ethyl acetate).
(3) 4-[(3-chloro-4-fluorophenyl)amino]-6-nitro-7-[(tetrahydrofuran-2-yl)methoxy]quinazoline Mass spectrum (ESI⁻): m/z=417, 419 [M–H]⁻; $R_f$ value: 0.47 (silica gel, ethyl acetate).
(4) 4-[(3-chloro-4-fluorophenyl)amino]-6-nitro-7-[(tetrahydrofuran-3-yl)methoxy]quinazoline Mass spectrum (ESI⁻): m/z=417, 419 [M–H]⁻; $R_f$ value: 0.41 (silica gel, ethyl acetate).
(5) 4-[(3-chloro-4-fluorophenyl)amino]-6-nitro-7-[(tetrahydropyran-4-yl)methoxy]quinazoline Mass spectrum (ESI⁺): m/z=433, 435 [M+H]⁺; $R_f$ value: 0.79 (silica gel, ethyl acetate/methanol=9:1).
(6) 4-[(3-chloro-4-fluorophenyl)amino]-6-nitro-7-[(R)-(tetrahydrofuran-2-yl)methoxy]quinazoline Mass spectrum (ESI⁺): m/z=419, 421 [M+H]⁺; $R_f$ value: 0.44 (silica gel, ethyl acetate).
(7) 4-[(3-chloro-4-fluorophenyl)amino]-6-nitro-7-[(S)-(tetrahydrofuran-2-yl)methoxy]quinazoline Mass spectrum (ESI⁺): m/z=419, 421 [M+H]⁺; $R_f$ value: 0.44 (silica gel, ethyl acetate).

EXAMPLE V
(R)-N-[(tetrahydrofuran-2-yl)methyl]-N-methylamine 21.10 g of (R)-N-[(tetrahydrofuran-2-yl)methyl]-N-benzyl-N-methylamine (crude product from Example VI) are dissolved in 200 ml of methanol and hydrogenated in the presence of 4.00 g of palladium on activated charcoal (10% Pd) at ambient temperature until the uptake of hydrogen has ended. For working up the catalyst is filtered off and the filtrate is evaporated using the rotary evaporator. A thin yellow oil is left, which is further reacted without any more purification. Yield: 8.60 g (73% of theory); mass spectrum (ESI⁺): m/z=116 [M+H]⁺.

The following compounds are obtained analogously to Example V:
(1) (S)-N-[(tetrahydrofuran-2-yl)methyl]-N-methylamine Mass spectrum (ESI⁺): m/z=116 [M+H]⁺.
(2) N-[(tetrahydropyran-4-yl)methyl]-N-methylamine Mass spectrum (ESI⁺): m/z=130 [M+H]⁺.

EXAMPLE VI
(R)-N-[(tetrahydrofuran-2-yl)methyl]-N-benzyl-N-methylamine

A solution of 24.60 g of (R)-tetrahydrofuran-2-carboxylic acid-N-benzyl-N-methylamide in 90 ml tetrahydrofuran is added dropwise to 17.00 g of lithium aluminium hydride in 150 ml of tetrahydrofuran. The reaction mixture is refluxed for two hours. For working up it is cooled to 0° C. in an ice bath, mixed with 20 ml of water and 10 ml of 15 N sodium hydroxide solution and stirred for another 20 minutes. Then it is filtered through a layer of magnesium sulfate and washed with a total of about 500 ml of tetrahydrofuran. The filtrate is evaporated down in vacuo, leaving a yellowish oil which is further reacted without any more purification. Yield: 21.10 g (92% of theory); mass spectrum (ESI⁺): m/z=206 [M+H]⁺.

The following compounds are obtained analogously to Example VI:
(1) (S)-N-[(tetrahydrofuran-2-yl)methyl]-N-benzyl-N-methylamine $R_f$ value: 0.20 (silica gel, ethyl acetate/methanol=9:1).
(2) N-[(tetrahydropyran-4-yl)methyl]-N-benzyl-N-methylamine Mass spectrum (ESI⁺): m/z=220 [M+H]⁺.

EXAMPLE VII
(R)-tetrahydrofuran-2-carboxylic acid-N-benzyl-N-methylamide 25.30 g of N-benzyl-N-methylamine are added to a solution of 20.00 ml of (R)-tetrahydrofuran-2-carboxylic acid in 200 ml tetrahydrofuran. Then a total of 67.10 g of O-(benzotriazol-1-yl)-N,N,N',N'-tetramethyluronium tetrafluoroborate are added batchwise while cooling with an ice bath and the reaction mixture is then stirred for about 48 hours at ambient temperature. The precipitate formed is suction filtered, the filtrate is evaporated, mixed with water and filtered again. The filtrate obtained is made alkaline with sodium hydrogen carbonate solution and extracted with ethyl acetate. The combined ethyl acetate extracts are washed with water and saturated sodium chloride solution, dried over magnesium sulfate, and evaporated down. A yellowish oil remains, which is further reacted without any further purification. Yield: 24.60 g (54% of theory); mass spectrum (ESI⁺): m/z=220 [M+H]⁺; $R_f$ value: 0.62 (silica gel, ethyl acetate).

The following compounds are obtained analogously to Example VII:
(1) (S)-tetrahydrofuran-2-carboxylic acid-N-benzyl-N-methylamide Mass spectrum (ESI⁺): m/z=242 [M+Na]⁺; $R_f$ value: 0.62 (silica gel, ethyl acetate).
(2) tetrahydropyran-4-carboxylic acid-N-benzyl-N-methylamide The amide coupling is carried out with 1,1'-carbonyldiimidazole in tetrahydrofuran. Mass spectrum (ESI⁺): m/z=256 [M+Na]⁺; $R_f$ value: 0.45 (silica gel, ethyl acetate).

EXAMPLE VIII
6-Amino-4-[(3-chloro-4-fluorophenyl)amino]-7-[(tetrahydropyran-4-yl)methoxy]quinazoline 22.80 g of 4-[(3-chloro-4-fluorophenyl)amino]-6-nitro-7-[(tetrahydropyran-4-yl)methoxy]quinazoline are hydrogenated in 300 ml of tetrahydrofuran in the presence of 3.50 g of platinum dioxide at ambient temperature until the calculated amount of hydrogen has been taken up. The catalyst is filtered off and the filtrate is evaporated to dryness using the rotary evaporator. The residue is stirred with diethylether, suction filtered, washed with diethylether and dried at ambient temperature. Yield: 19.95 g (93% of theory); mass spectrum (ESI$^+$): m/z=403, 405 [M+H]$^+$; melting point: 221° C.

The following compounds are obtained analogously to Example VIII:
(1) 6-Amino-4-[(3-chloro-4-fluorophenyl)amino]-7-[(R)-(tetrahydrofuran-2-yl)methoxy]quinazoline
Mass spectrum (ESI$^+$): m/z=389, 391 [M+H]$^+$; $R_f$ value: 0.11 (silica gel, ethyl acetate).
(2) 6-Amino-4-[(3-chloro-4-fluorophenyl)amino]-7-[(S)-(tetrahydrofuran-2-yl)methoxy]quinazoline
Mass spectrum (ESI$^+$): m/z=389, 391 [M+H]$^+$; $R_f$ value: 0.33 (silica gel, ethyl acetate/methanol=9:1).

Preparation of the Final Compounds

EXAMPLE 1

4-[(3-chloro-4-fluorophenyl)amino]-6-({4-[N-(2-methoxyethyl)-N-methylamino]-1-oxo-2-buten-1-yl}amino)-7-cyclopropylmethoxyquinazoline 4.70 ml of oxalyl chloride are added dropwise to a solution of 4.50 g of bromocrotonic acid in 60 ml of methylene chloride. Then one drop of N,N-dimethylformamide is added. After about 30 minutes, the development of gas has ended and the reaction mixture is evaporated using the rotary evaporator. The crude bromocrotonic acid chloride is taken up in 30 ml of methylene chloride and, while cooling with an ice bath, added dropwise to a solution of 7.00 g of 4-[(3-chloro-4-fluorophenyl)amino]-6-amino-7-cyclopropylmethoxyquinazoline and 10.20 ml of Hünig base in 150 ml of tetrahydrofuran. The reaction mixture is stirred for about 1.5 hours while cooling with an ice bath and then for another two hours at ambient temperature. Then 5.20 g of N-(2-methoxyethyl)-N-methylamine are added and the reaction mixture is stirred overnight at ambient temperature. For working up, it is diluted with methylene chloride and washed thoroughly with water. The organic phase is dried over magnesium sulfate and evaporated down. The crude product is purified by chromatography over a silica gel column with ethyl acetate followed by ethyl acetate/methanol (19:1) as eluant. Yield: 5.07 g (51% of theory); mass spectrum (ESI$^-$): m/z=512, 514 [H–H]$^-$; $R_f$ value: 0.25 (silica gel, ethyl acetate/methanol=9:1).

The following compounds are obtained analogously to Example 1:
(1) 4-[(3-chloro-4-fluorophenyl)amino]-6-{[4-(N,N-dimethylamino)-1-oxo-2-buten-1-yl]amino}-7-cyclobutyloxyquinazoline
Mass spectrum (ESI$^-$): m/z=468, 470 [M–H]$^-$; $R_f$ value: 0.09 (silica gel, ethyl acetate/methanol=9:1).
(2) 4-[(3-chloro-4-fluorophenyl)amino]-6-{[4-(N,N-dimethylamino)-1-oxo-2-buten-1-yl]amino}-7-cyclopentyloxyquinazoline
Mass spectrum (ESI$^-$): m/z=482, 484 [M–H]$^-$; $R_f$ value: 0.11 (silica gel, ethyl acetate/methanol=9:1).
(3) 4-[(R)-(1-phenylethyl)amino]-6-{[4-(N,N-bis(2-methoxyethyl)amino)-1-oxo-2-buten-1-yl]amino}-7-cyclopropylmethoxyquinazoline
Mass spectrum (ESI$^-$): m/z=532 [M–H]$^-$; $R_f$ value: 0.40 (silica gel, ethyl acetate/methanol=9:1).
(4) 4-[(R)-(1-phenylethyl)amino]-6-({4-[N-(2-methoxyethyl)-N-ethylamino]-1-oxo-2-buten-1yl}amino)-7-cyclopropylmethoxyquinazoline
Mass spectrum (ESI$^-$): m/z=502 [M–H]$^-$; $R_f$ value: 0.20 (silica gel, ethyl acetate/methanol=9:1).
(5) 4-[(R)-(1-phenylethyl)amino]-6-({4-[N-(2-methoxyethyl)-N-methylamino]-1-oxo-2-buten-1-yl}amino)-7-cyclopropylmethoxyquinazoline
Mass spectrum (ESI$^-$): m/z=488 [M–H]$^-$; $R_f$ value: 0.25 (silica gel, ethyl acetate/methanol=9:1).
(6) 4-[(R)-(1-phenylethyl)amino]-6-({4-[N-(tetrahydropyran-4-yl)-N-methylamino]-1-oxo-2-buten-1-yl}amino)-7-cyclopropylmethoxyquinazoline
Mass spectrum (ESI$^-$): m/z=514 [H–H]$^-$; $R_f$ value: 0.15 (silica gel, ethyl acetate/methanol=9:1).
(7) 4-[(R)-(1-phenylethyl)amino]-6-({4-[N-(tetrahydrofuran-3-yl)-N-methylamino]-1-oxo-2-buten-1-yl}amino)-7-cyclopropylmethoxyquinazoline
Mass spectrum (ESI$^-$): m/z=500 [M–H]$^-$; $R_f$ value: 0.18 (silica gel, ethyl acetate/methanol=9:1).
(8) 4-[(3-chloro-4-fluorophenyl)amino]-6-[(4-{N-[(tetrahydrofuran-3-yl)methyl]-N-methylamino}-1-oxo-2-buten-1-yl)amino]-7-cyclopropylmethoxyquinazoline
Mass spectrum (ESI$^-$): m/z=538, 540 [M–H]$^-$; $R_f$ value: 0.27 (silica gel, ethyl acetate/methanol=9:1).
(9) 4-[(3-chloro-4-fluorophenyl)amino]-6-{[4-(N,N-dimethylamino)-1-oxo-2-buten-1-yl]amino}-7-((R)-tetrahydrofuran-3-yloxy)quinazoline; mass spectrum (ESI$^+$): m/z=486, 488 [M+H]$^+$.
(10) 4-[(3-chloro-4-fluorophenyl)amino]-6-{[4-(N,N-dimethylamino)-1-oxo-2-buten-1-yl]amino}-7-((S)-tetrahydrofuran-3-yloxy)quinazoline
Mass spectrum (ESI$^+$): m/z=486, 488 [M+H]$^+$; $R_f$ value: 0.45 (silica gel, methylene chloride/methanol=5:1).
(11) 4-[(3-chloro-4-fluorophenyl)amino]-6-{[4-(N,N-dimethylamino)-1-oxo-2-buten-1-yl]amino}-7-(tetrahydropyran-4-yloxy)quinazoline
Mass spectrum (ESI$^+$): m/z=500, 502 [M+H]$^+$; $R_f$ value: 0.55 (silica gel, methylene chloride/methanol=5:1).
(12) 4-[(3-chloro-4-fluorophenyl)amino]-6-{[4-(N,N-dimethylamino)-1-oxo-2-buten-1-yl]amino}-7-[(tetrahydrofuran-2-yl)methoxy]quinazoline
Mass spectrum (ESI$^+$): m/z=500, 502 [M+H]$^+$; $R_f$ value: 0.60 (silica gel, methylene chloride/methanol=5:1).
(13) 4-[(3-chloro-4-fluorophenyl)amino]-6-{[4-(N,N-dimethylamino)-1-oxo-2-buten-1-yl]amino}-7-[(tetrahydrofuran-3-yl)methoxy]quinazoline
Mass spectrum (ESI$^+$): m/z=500, 502 [M+H]$^+$; $R_f$ value: 0.50 (silica gel, methylene chloride/methanol=5:1).
(14) 4-[(3-chloro-4-fluorophenyl)amino]-6-{[4-(N,N-diethylamino)-1-oxo-2-buten-1-yl]amino}-7-[(tetrahydrofuran-3-yl)methoxy]quinazoline
Mass spectrum (ESI$^+$): m/z=528, 530 [M+H]$^+$; $R_f$ value: 0.31 (silica gel, ethyl acetate/methanol=9:1).
(15) 4-[(R)-(1-phenylethyl)amino]-6-{[4-(N,N-dimethylamino)-1-oxo-2-buten-1-yl]amino}-7-cyclopropylmethoxyquinazoline
Mass spectrum (ESI$^+$): m/z=446 [M+H]$^+$; $R_f$ value: 0.11 (silica gel, ethyl acetate/methanol=9:1).
(16) 4-[(3-chloro-4-fluorophenyl)amino]-6-({4-[N,N-bis(2-methoxyethyl)amino]-1-oxo-2-buten-1-yl}amino)-7-[(tetrahydrofuran-2-yl)methoxy]quinazoline
Mass spectrum (ESI$^+$): m/z=588, 590 [M+H]$^+$; $R_f$ value: 0.55 (silica gel, methylene chloride/methanol=9:1).
(17) 4-[(3-chloro-4-fluorophenyl)amino]-6-{[4-(morpholin-4-yl)-1-oxo-2-buten-1-yl]amino}-7-[(tetrahydrofuran-2-yl)methoxy]quinazoline
Mass spectrum (ESI$^+$): m/z=542, 544 [M+H]$^+$; $R_f$ value: 0.55 (silica gel, methylene chloride/methanol=9:1).
(18) 4-[(3-chloro-4-fluorophenyl)amino]-6-({4-[N-(2-methoxyethyl)-N-methylamino]-1oxo-2-buten-1-yl}amino)-7-cyclopentyloxyquinazoline
Mass spectrum (ESI$^+$): m/z=528, 530 [M+H]$^+$; $R_f$ value: 0.25 (silica gel, ethyl acetate/methanol=9:1).
(19) 4-[(3-chloro-4-fluorophenyl)amino]-6-[(4-{(R)-N-[(tetrahydrofuran-2-yl)methyl]-N-methylamino}1-oxo-2-buten-1-yl)amino]-7-cyclopropylmethoxyquinazoline
Mass spectrum (ESI$^+$): m/z=540, 542 [M+H]$^+$; melting point: 149° C.–153° C.

(20) 4-[(3-chloro-4-fluorophenyl)amino]-6-[(4-{(S)-N-[(tetrahydrofuran-2-yl)methyl]-N-methylamino}-1-oxo-2-buten-1-yl)amino]-7-cyclopropylmethoxyquinazoline
Mass spectrum (ESI$^+$): m/z=540, 542 [M+H]$^+$; R$_f$ value: 0.29 (silica gel, ethyl acetate/methanol=9:1).

(21) 4-[(R)-(1-phenylethyl)amino]-6-{[4-(N,N-dimethylamino)-1-oxo-2-buten-1-yl]amino}-7-cyclopentyloxyquinazoline
Mass spectrum (ESI$^+$): m/z=560 [M+H]$^+$; R$_f$ value: 0.17 (silica gel, ethyl acetate/methanol=9:1).

(22) 4-[(3-chloro-4-fluorophenyl)amino]-6-{[4-(N-cyclopropyl-N-methylamino)-1-oxo-2-buten-1-yl]amino}-7-cyclopentyloxyquinazoline
Mass spectrum (ESI$^-$): m/z=508, 510 [M−H]$^-$; melting point: 140° C.

(23) 4-[(3-chloro-4-fluorophenyl)amino]-6-{[4-(N-cyclopropyl-N-methylamino)-1-oxo-2-buten-1-yl]amino}-7-cyclopropylmethoxyquinazoline
Mass spectrum (ESI$^+$): m/z=496, 498 [M+H]$^+$; R$_f$ value: 0.42 (silica gel, ethyl acetate/methanol=9:1).

(24) 4-[(3-chloro-4-fluorophenyl)amino]-6-[(4-{N-[(tetrahydropyran-4-yl)methyl]-N-methylamino}-1-oxo-2-buten-1-yl)amino]-7-cyclopropylmethoxyquinazoline
Mass spectrum (ESI$^+$): m/z=554, 556 [M+H]$^+$; melting point: 141° C.

(25) 4-[(R)-(1-phenylethyl)amino]-6-[(4-{N-[(tetrahydropyran-4-yl)methyl]-N-methylamino}1-oxo-2-buten-1-yl)amino]-7-cyclopropylmethoxyquinazoline
Mass spectrum (ESI$^+$): m/z=530 [M+H]$^+$; R$_f$ value: 0.32 (silica gel, ethyl acetate/methanol/conc. aqueous ammonia=90:10:0.5).

(26) 4-[(3-chloro-4-fluorophenyl)amino]-6-[(4-{(R)-N-[(tetrahydrofuran-2-yl)methyl]-N-methylamino}-1-oxo-2-buten-1-yl)amino]-7-cyclopentyloxyquinazoline
Mass spectrum (ESI$^+$): m/z=554, 556 [M+H]$^+$; melting point: 117° C.–121° C.

(27) 4-[(3-chloro-4-fluorophenyl)amino]-6-[(4-{(S)-N-[(tetrahydrofuran-2-yl)methyl]-N-methylamino}-1-oxo-2-buten-1-yl)amino]-7-cyclopentyloxyquinazoline
Mass spectrum (ESI$^+$): m/z=554, 556 [M+H]$^+$; R$_f$ value: 0.32 (silica gel, ethyl acetate/methanol/conc. aqueous ammonia=90:10:0.5).

(28) 4-[(3-chloro-4-fluorophenyl)amino]-6-{[4-(N,N-dimethylamino)-1-oxo-2-buten-1-yl]amino}-7-[(tetrahydropyran-4-yl)methoxy]quinazoline
Mass spectrum (ESI$^+$): m/z=514, 516 [M+H]$^+$; R$_f$ value: 0.19 (silica gel, methylene chloride/methanol/conc. aqueous ammonia=95:5:0.05).

(29) 4-[(3-chloro-4-fluorophenyl)amino]-6-{[4-(morpholin-4-yl)-1-oxo-2-buten-1-yl]amino}7-[(tetrahydropyran-4-yl)methoxy]quinazoline
Mass spectrum (ESI$^-$): m/z=554, 556 [M−H]$^-$; melting point: 174° C.

(30) 4-[(3-chloro-4-fluorophenyl)amino]-6-({4-[N,N-bis(2-methoxyethyl)amino]-1-oxo-2-buten-1-yl}amino)-7-[(tetrahydropyran-4-yl)methoxy]quinazoline
Mass spectrum (ESI$^+$): m/z=602, 604 [M+H]$^+$; melting point: 100° C.–102° C.

(31) 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]quinazoline
Mass spectrum (ESI$^+$): m/z=500, 502 [M+H]$^+$; melting point: 110° C.–112° C.

(32) 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]quinazoline
Mass spectrum (ESI$^+$): m/z=500, 502 [M+H]$^+$; R$_f$ value: 0.23 (silica gel, ethyl acetate/methanol/conc. aqueous ammonia=90:10:0.1).

(33) 4-[(3-chloro-4-fluorophenyl)amino]-6-{[4-(N-ethyl-N-methylamino)-1-oxo-2-buten-1-yl]amino}-7-[(S)-(tetrahydrofuran-3-yl)oxy]quinazoline
Mass spectrum (ESI$^+$): m/z=500, 502 [M+H]$^+$; melting point: 154° C.–157° C.

(34) 4-[(3-chloro-4-fluorophenyl)amino]-6-{[4-(N-isopropyl-N-methylamino)-1-oxo-2-buten-1-yl]amino}-7-[(S)-(tetrahydrofuran-3-yl)oxy]quinazoline
Mass spectrum (ESI$^+$): m/z=514, 516 [M+H]$^+$; R$_f$ value: 0.34 (silica gel, ethyl acetate/methanol/conc. aqueous ammonia=90:10:1).

(35) 4-[(3-chloro-4-fluorophenyl)amino]-6-{[4-(morpholin-4-yl)-1-oxo-2-buten-1-yl]amino}-7-[(S)-(tetrahydrofuran-3-yl)oxy]quinazoline
Mass spectrum (ESI$^+$): m/z=528, 530 [M+H]$^+$; melting point: 184° C.–185° C.

(36) 4-[(3-chloro-4-fluorophenyl)amino]-6-{[4-(N-isopropyl-N-methylamino)-1-oxo-2-buten-1-yl]amino}-7-cyclopentyloxyquinazoline
Mass spectrum (ESI$^+$): m/z=512, 514 [M+H]$^+$; R$_f$ value: 0.53 (silica gel, ethyl acetate/methanol/conc. aqueous ammonia=90:10:0.5).

(37) 4-[(3-chloro-4-fluorophenyl)amino]-6-{[4-(N-ethyl-N-methylamino)-1-oxo-2-buten-1-yl]amino}-7-[(S)-(tetrahydrofuran-2-yl)methoxy]quinazoline
Mass spectrum (ESI$^-$): m/z=512, 514 [M−H]$^-$; R$_f$ value: 0.15 (silica gel, ethyl acetate/methanol/conc. aqueous ammonia=90:10:1).

(38) 4-[(3-chloro-4-fluorophenyl)amino]-6-{[4-(N,N-diethylamino)-1-oxo-2-buten-1-yl]amino}-7-[(S)-(tetrahydrofuran-2-yl)methoxy]quinazoline
Mass spectrum (ESI$^-$): m/z=526, 528 [M−H]$^-$; R$_f$ value: 0.27 (silica gel, methylene chloride/methanol=9:1).

(39) 4-[(3-chloro-4-fluorophenyl)amino]-6-{[4-(N-isopropyl-N-methylamino)-1-oxo-2-butene-1-yl]amino}-7-[(S)-(tetrahydrofuran-2-yl)methoxy]quinazoline
Mass spectrum (ESI$^+$): m/z=528, 530 [M+H]$^+$; R$_f$ value: 0.31 (silica gel, methylene chloride/methanol=9:1).

The following compounds may also be prepared analogously to the foregoing Examples and other methods known from the literature:

(1) 4-benzylamino-6-{[4-(N,N-diethylamino)-1-oxo-2-buten-1-yl]amino}-7-cyclopropylmethoxyquinazoline (2) 4-[(3-chloro-4-fluorophenyl)amino]-6-[(4-{N-[(tetrahydropyran-4-yl)methyl]-N-methylamino}-1-oxo-2-buten-1-yl)amino]-7-cyclopropylmethoxyquinazoline (3) 4-[(3-chloro-4-fluorophenyl)amino]-6-{[4-(N,N-dimethylamino)-1-oxo-2-buten-1-yl]amino}-7-[(tetrahydropyran-4-yl)methoxy]quinazoline (4) 4-[(R)-(1-phenylethyl)amino]-6-[(4-{N-[(tetrahydrofuran-2-yl)methyl]-N-methylamino}1-oxo-2-buten-1-yl)amino]-7-cyclopropylmethoxyquinazoline (5) 4-[(R)-(1-phenylethyl)amino]-6-{[4-(N,N-dimethylamino)-1-oxo-2-buten-1-yl]amino}-7-[(tetrahydrofuran-2-yl)methoxy]quinazoline (6) 4-[(R)-(1-phenylethyl)amino]-6-({4-[N,N-bis(2-methoxyethyl)amino]-1-oxo-2-buten-1-yl}amino)-7-[(tetrahydrofuran-2-yl)methoxy]quinazoline (7) 4-[(R)-(1-phenylethyl)amino]-6-{[4-(morpholin-4-yl)-1-oxo-2-buten-1-yl]amino}-7-[(tetrahydrofuran-2-yl)methoxy]quinazoline

EXAMPLE 2

| Coated tablets containing 75 mg of active substance | |
| --- | --- |
| 1 tablet core contains: | |
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
|  | 230.0 mg |

Preparation

The active substance is mixed with calcium phosphate, corn starch, polyvinylpyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape. Weight of core: 230 mg; die: 9 mm, convex. The tablet cores thus produced are coated with a film consisting essentially of hydroxypropylmethylcellulose. The finished film-coated tablets are polished with beeswax. Weight of coated tablet: 245 mg.

EXAMPLE 3

| Tablets containing 100 mg of active substance | |
| --- | --- |
| Composition: 1 tablet contains: | |
| active substance | 100.0 mg |
| lactose | 80.0 mg |
| corn starch | 34.0 mg |
| polyvinylpyrrolidone | 4.0 mg |
| magnesium stearate | 2.0 mg |
|  | 220.0 mg |

Preparation

The active substance, lactose and starch are mixed together and uniformly moistened with an aqueous solution of the polyvinylpyrrolidone. After the moist composition has been screened (2.0 mm mesh size) and dried in a rack-type drier at 50° C., it is screened again (1.5 mm mesh size) and the lubricant is added. The finished mixture is compressed to form tablets. Weight of tablet: 220 mg; diameter: 10 mm, biplanar, facetted on both sides and notched on one side.

EXAMPLE 4

| Tablets containing 150 mg of active substance | |
| --- | --- |
| Composition: 1 tablet contains: | |
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
|  | 300.0 mg |

Preparation

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture. Weight of tablet: 300 mg; die: 10 mm, flat.

EXAMPLE 5

| Hard gelatine capsules containing 150 mg of active substance | |
| --- | --- |
| 1 capsule contains: | |
| active substance | 50.0 mg |
| corn starch (dried) | approx. 80.0 mg |
| lactose (powdered) | approx. 87.0 mg |
| magnesium stearate | 3.0 mg |
|  | approx. 420.0 mg |

Preparation

The active substance is mixed with the excipients, passed through a screen with a mesh size of 0.75 mm and homogeneously mixed using a suitable apparatus. The finished mixture is packed into size 1 hard gelatine capsules. Capsule filling: approx. 320 mg; capsule shell: size 1 hard gelatine capsule.

EXAMPLE 6

| Suppositories containing 150 mg of active substance | |
| --- | --- |
| 1 suppository contains: | |
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
|  | 2,000.0 mg |

Preparation

After the suppository mass has been melted, the active substance is homogeneously distributed therein and the melt is poured into chilled molds.

EXAMPLE 7

| Suspension containing 50 mg of active substance | |
| --- | --- |
| 100 ml of suspension contains: | |
| active substance | 1.00 g |
| carboxymethylcellulose-Na-salt | 0.10 g |

-continued

| Suspension containing 50 mg of active substance | |
|---|---|
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavoring | 0.30 g |
| dist. water | ad 100 ml |

Preparation

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution, and the flavoring have been added and dissolved, the suspension is evacuated with stirring to eliminate air. 5 ml of suspension contains 50 mg of active substance.

EXAMPLE 8

| Ampoules containing 10 mg active substance | |
|---|---|
| Composition: | |
| active substance | 10.0 mg |
| 0.01 N hydrochloric acid | q.s. |
| double-distilled water | ad 2.0 ml |

Preparation

The active substance is dissolved in the requisite amount of 0.01 N HCl, made isotonic with common salt, filtered sterile and transferred into 2 ml ampoules.

EXAMPLE 9

| Ampoules containing 50 mg of active substance | |
|---|---|
| Composition: | |
| active substance | 50.0 mg |
| 0.01 N hydrochloric acid | q.s. |
| double-distilled water | ad 10.0 ml |

Preparation

The active substance is dissolved in the necessary amount of 0.01 N HCl, made isotonic with common salt, filtered sterile and transferred into 10 ml ampoules.

EXAMPLE 10

| Capsules for powder inhalation containing 5 mg of active substance | |
|---|---|
| 1 capsule contains: | |
| active substance | 5.0 mg |
| lactose for inhalation | 15.0 mg |
| | 20.0 mg |

Preparation

The active substance is mixed with lactose for inhalation. The mixture is packed into capsules in a capsule-making machine (weight of the empty capsule approx. 50 mg). Weight of capsule: 70.0 mg; size of capsule: 3.

EXAMPLE 11

| Solution for inhalation for hand-held nebulizers containing 2.5 mg active substance | |
|---|---|
| 1 spray contains: | |
| active substance | 2.500 mg |
| benzalkonium chloride | 0.001 mg |
| 1 N hydrochloric acid | q.s. |
| ethanol/water (50/50) | ad 15.000 mg |

Preparation

The active substance and benzalkonium chloride are dissolved in ethanol/water (50/50). The pH of the solution is adjusted with 1N hydrochloric acid. The resulting solution is filtered and transferred into suitable containers for use in hand-held nebulizers (cartridges). Contents of the container: 4.5 g.

We claim:

1. A compound of formula I

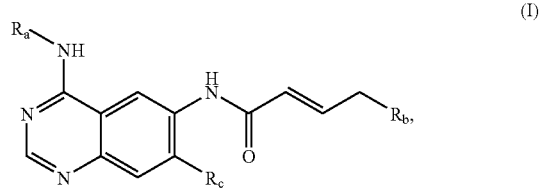

wherein $R_a$ is a benzyl, 1-phenylethyl, or 3-chloro-4-fluorophenyl group;

$R_b$ is a dimethylamino, N-methyl-N-ethylamino, N-methyl-N-isopropylamino, N-methyl-N-cyclopropylamino, N-methyl-N-(2-methoxyethyl)amino, N-ethyl-N-(2-methoxyethyl)amino, bis(2-methoxyethyl)amino, morpholino, N-methyl-N-(tetrahydrofuran-3-yl)amino, N-methyl-N-(tetrahydrofuran-2-ylmethyl)amino, N-methyl-N-(tetrahydrofuran-3-ylmethyl)amino, N-methyl-N-(tetrahydropyran-4-yl)amino, or N-methyl-N-(tetrahydropyran-4-ylmethyl)amino group; and $R_c$ is a cyclopropylmethoxy, cyclobutyloxy, cyclopentyloxy, tetrahydrofuran-3-yloxy, tetrahydrofuran-2-ylmethoxy, tetrahydrofuran-3-ylmethoxy, tetrahydropyran-4-yloxy, or tetrahydropyran-4-ylmethoxy group, or a stereoisomer or physiologically acceptable salt thereof.

2. The compound of claim 1, wherein Rb is a dimethylamino or a stereoisomer or physiologically acceptable salt thereof.

3. The compound of formula I according to claim 1, wherein:

$R_a$ is a 1-phenylethyl or 3-chloro-4-fluorophenyl group;

$R_b$ is a dimethylamino, N-methyl-N-ethylamino, N-methyl-N-isopropylamino, N-methyl-N-cyclopropylamino, N-methyl-N-(2-methoxyethyl)amino, N-ethyl-N-(2-methoxyethyl)amino, bis(2- methoxyethyl)amino, morpholino, N-methyl-N-(tetrahydrofuran-3-yl)amino, N-methyl-N-(tetrahydrofuran-2-ylmethyl)amino, N-methyl-N-(tetrahydrofuran-3-ylmethyl)amino, N-methyl-N-(tetrahydropyran-4-yl)amino, or N-methyl-N-(tetrahydropyran-4-ylmethyl)amino group; and $R_c$ is a cyclopropylmethoxy, cyclobutyloxy, cyclopentyloxy, tetrahydrofuran-3-yloxy, tetrahydrofuran-2-ylmethoxy, tetradrofuran-3-ylmethoxy, tetrahydropyran-4-yloxy, or tetrahydropyran-4-ylmethoxy group, or a stereoisomer or physiologically acceptable salt thereof.

4. The compounds of claim 3, wherein $R_b$ is a dimethylamino, or a stereoisomer or physiologically acceptable salt thereof.

5. The compounds of claim 3, wherein $R_a$ is a 3-chloro-4-fluorohenyl group and $R_b$ is a dimethylamino group, or a stereoisomer or physiologically acceptable salt thereof.

6. The compound of formula I according to claim 1, wherein:

$R_a$ is a 3-chloro-4-fluorophenyl group;

$R_b$ is a dimethylaminno group; and $R_c$ is a tetrahydrofuran-3-yloxy, tetrahydrofuran-2-ylmethoxy, tetrahydrofuran-3-ylmethoxy, tetrahydropyran-4-yloxy, or tetrahydropyran-4-ylmethoxy group, or a steroisomer or physiologically acceptable salt thereof.

* * * * *